(12) United States Patent
Creighton, IV

(10) Patent No.: US 7,662,126 B2
(45) Date of Patent: Feb. 16, 2010

(54) ULTRASONIC DISBURSEMENT OF MAGNETICALLY DELIVERED SUBSTANCES

(75) Inventor: Francis M. Creighton, IV, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 613 days.

(21) Appl. No.: 11/514,690

(22) Filed: Sep. 1, 2006

(65) Prior Publication Data

US 2007/0055130 A1    Mar. 8, 2007

Related U.S. Application Data

(60) Provisional application No. 60/714,088, filed on Sep. 2, 2005.

(51) Int. Cl.
*A61B 17/20* (2006.01)
(52) U.S. Cl. .................. 604/22; 604/510; 604/95.05
(58) Field of Classification Search ............... 604/19, 604/20, 22, 500, 501, 506, 507, 508, 510, 604/95.01, 95.05
See application file for complete search history.

(56) References Cited

U.S. PATENT DOCUMENTS 5,067,952 A * 11/1991 Gudov et al. ............... 606/28

2006/0216275 A1    9/2006  Mon .................. 424/93.2
2007/0093744 A1 *  4/2007  Elmaleh ................ 604/22

* cited by examiner

*Primary Examiner*—Kevin C Sirmons
*Assistant Examiner*—Bhisma Mehta
(74) *Attorney, Agent, or Firm*—Harness, Dickey & Pierce, P.L.C.

(57) ABSTRACT

A system and method are provided for attracting a magnetically responsive substance inserted in a subject's body towards a target area within the body to treat the area. The system generally comprises a medical device having a proximal end, a distal end, and at least one magnetic element disposed at the distal end of the medical device for orienting the distal end in a desired direction to place an aperture against the opposite wall of the vessel. The system further includes a voltage that may be applied to a coil that is disposed on the side of the medical device and proximally spaced from the magnetic element. A voltage is applied to the coil to attract the magnetically responsive substances inserted into the body around the coil. A high frequency alternating current voltage is applied to an adjacent transducer to ultrasonically disperse the collected magnetically responsive substances into the surrounding target tissue.

20 Claims, 4 Drawing Sheets

ULTRASONIC DISBURSEMENT OF MAGNETICALLY DELIVERED SUBSTANCES

FIELD OF THE INVENTION

The present invention relates to delivery of substances to target areas within a subject body, and more particularly to percutaneous transluminal procedures for the targeted delivery of substances.

BACKGROUND OF THE INVENTION

Interventional medicine is the collection of medical procedures in which access to the site of treatment is made through one of the patient's blood vessels, body lumens or cavities. For example, treatment of vascular defects may be performed using a catheter which enters the patient's arterial system through a puncture of an artery, and is referred to as a Percutaneous (through the skin), Transluminal (through the blood vessel) procedure. The heretofore major impediment to particle drug delivery through the vasculature has been an inability to retain a significant fraction of the particles at the site where needed, because of the dominant viscous forces acting to rapidly drag the particles downstream in vessels with blood flowing rapidly. Even with the highest magnetic gradients available and the largest practical magnetic particles the effective delivery at the point of interest has been fractions of a percent for velocities found in all vasculatures of the body butt the capillaries. Moreover, delivery of various medical substances through the tenuous vascular wall can be difficult.

Interventional medicine is the collection of medical procedures in which access to the site of treatment is made through one of the patient's blood vessels, body cavities or lumens. For example, treatment of vascular defects may be performed using a catheter which enters the patient's arterial system through a puncture of an artery, and is referred to as a Percutaneous (through the skin), Transluminal (through the blood vessel) procedure. The heretofore major impediment to particle drug delivery through the vasculature has been an inability to retain a significant fraction of the particles at the site where needed, because of the dominant viscous forces acting to rapidly drag the particles downstream in vessels with blood flowing rapidly. Even with the highest magnetic gradients available and the largest practical magnetic particles the effective delivery at the point of interest has been fractions of a percent for velocities found in all vasculatures except the capillaries of the body. Moreover, delivery of various medical substances through the tenuous vascular wall can be difficult.

SUMMARY OF THE INVENTION

Embodiments of the present invention provide a system and method for delivery of a magnetically responsive substance to a desired target area within a subject body. A catheter is inserted in the body vasculature and navigated to the target area, briefly held against the vascular wall, and a magnetically responsive substance is inserted through the catheter into the subject's body, and then attracted towards the target area through an aperture in the catheter. In one embodiment, a system is provided for attracting a magnetically responsive substance that is inserted into a subject's body towards a target area to treat the target area within the body with the magnetically responsive substance. The system generally includes an elongate medical device (preferably a catheter) having a proximal end, a distal end, and at least one magnetically responsive element disposed at the distal end of the medical device that may be oriented in a desired direction by an external magnetic field. The system further includes a coil disposed on the side of the elongate medical device that is spaced proximally from the distal end of the device. The coil faces an aperture in the elongate medical device. Within the catheter and attached to or near to the coil, and in a plane approximately parallel to the coil is an ultrasound transducer. The system further includes leads for applying a direct current voltage that may be applied to the coil. A direct current voltage may be applied to the coil to attract and preferentially collect magnetically responsive substances inserted into the body around the coil. Upon collecting a sufficient amount of the magnetically responsive substance around the coil, a high frequency alternating current voltage may be applied to the attached transducer to ultrasonically disperse the collected magnetically responsive substances into the tissue adjacent to the coil.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE EMBODIMENTS

The following descriptions of the various embodiments are merely exemplary in nature and are in no way intended to limit the invention, its application, or uses.

Embodiments of the present invention provide for delivery of a magnetically responsive substance to a desired target area within a subject body, where the magnetically responsive substance may be inserted within an elongated medical device into the subject's body and then migrated towards the target area. In one embodiment, a system is provided for introducing a magnetically responsive substance into a subject's body towards a target area to treat the target area within the body with the magnetically responsive substance. The system generally comprises an elongate medical device having a proximal end, a distal end, and at least one magnetically responsive element disposed at the distal end of the medical device that may be oriented in a desired direction by an external magnetic field applied to the distal end of the medical device. The system further comprises a coil disposed on the side of the elongate medical device, the coil being spaced proximally from the distal end so as to reduce interference from the external magnetic field applied to the magnetically responsive element. In this embodiment, the coil is disposed in a recessed area on the side of the elongate medical device, which recessed area also serves as a staging area for disbursement of the substance into the target tissue. The system further contains a disk-like transducer for generating ultrasound waves into the aperture through which the substance is passed to the wall of the blood vessel. In other embodiments, the coil and transducer may be separate components that are inserted or assembled into a conventional magnetically navigable catheter device. The system further comprises a direct current or low frequency alternating current voltage source (a), a high frequency alternating current source (b), and a control device for controlling the application of voltage (a) to the coil and the application of high frequency voltage (b) to the ultrasound transducer. The control device accordingly may apply a voltage (a) to the coil to attract and collect magnetically responsive substances inserted into the catheter around the coil. Upon collecting a sufficient amount of the magnetically responsive substance around the coil, the control device may then apply a high frequency alternating current voltage to the transducer to ultrasonically transfect the collected magnetically responsive substances into the tissue surrounding the coil.

Figure 1:
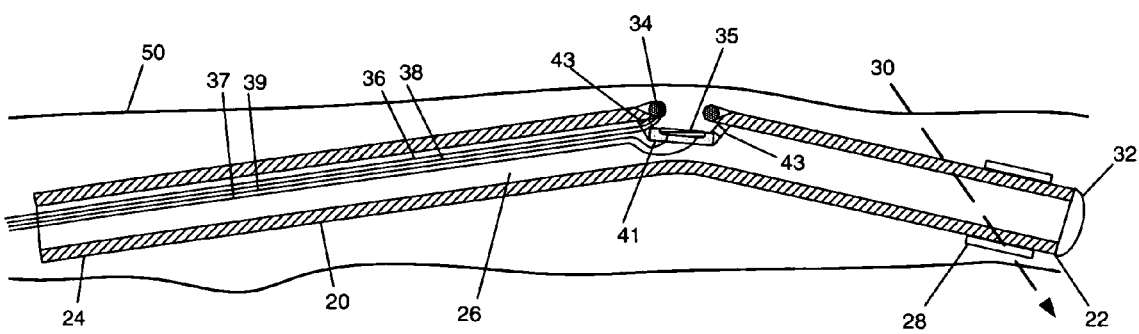
FIG. 1 shows a cross-sectional view of a medical device within a vessel of a subject body, with a coil and ultrasound transducer associated with the medical device for delivery of substances to a target area within the subject's body.
Figure 2:
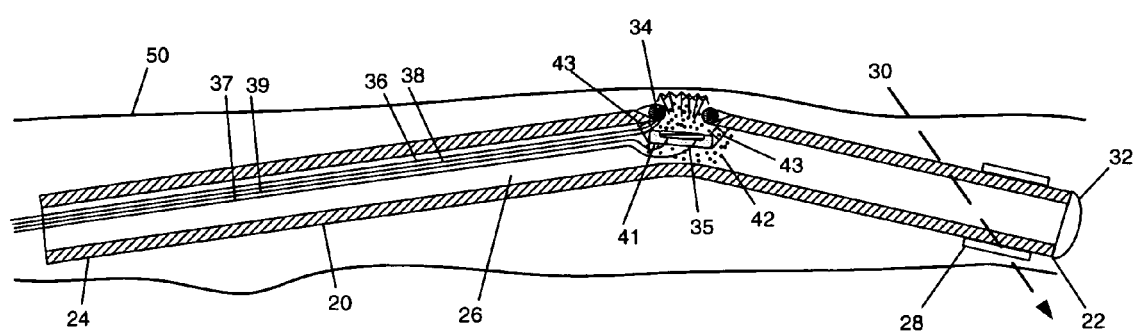
FIG. 2 shows a cross-sectional view of a medical device within a vessel of a subject body, with a magnetically responsive substance collected around the coil for dispersion.

Referring to FIG. 1, an elongate medical device 20 is depicted within a vessel 50 of a subject body's vasculature system. The elongate medical device 20 has a magnetic tip element 28 disposed near the distal end of the device 20, which is responsive to a magnetic field 30 applied external from the subject body or patient to orient the distal end of the medical device 20. The direction of the applied magnetic field 30 responsively causes the magnetic element 28 to orient the distal end of medical device 20 into the configuration shown in FIG. 1, due to the magnetic moment. In this position, the portion of the elongate medical device 20 opposite the direction of the tip bending and that includes the coil 34 is forced against the side wall of the vessel. In this embodiment, the coil 34 is spaced from the magnetic element 28 by a distance that is effective to minimize interference with the magnetic field of the magnetic tip element. When a DC (or in some cases AC) voltage is applied to the coil 34, the coil generates a field that attracts a magnetically responsive substance 42 that may be inserted within the catheter, where an outlet 40 adjacent the coil 34 as shown in FIG. 1 provides for injecting the magnetically responsive substance 42 through the coil and into the patient's vasculature. In this embodiment, the magnetically responsive substance 42 as shown in FIG. 2 is comprised of micro-bubbles that may be injected into the subject body's vasculature system. The micro-bubbles 42 are configured to hold a substance to be delivered to a target location within the subject body, as well as a magnetically responsive material of a quantity sufficient to permit the micro-bubble 42 to be attracted by a magnetic field. Upon application of ultrasound pulses of selected frequencies and sufficient power the micro-bubble will destruct and the enclosed substances will be projected into the surrounding tissue. This mechanism is especially advantageous for the delivery of substances to target areas such as vessel walls, which have a tenuous inner surface that is not easily penetrated. The ultrasound burst that destructs the micro-bubbles will also project the substances within the micro-bubble towards and through the surrounding tissue, a process called transfection. The ultrasound disbursement of the magnetically responsive substances accordingly provides for improved delivery of substances to target tissues within a subject's body.

In various embodiments of a system for delivering a substance within a subject body, the coil 34 is used to attract the magnetically responsive substance 42, and to collect or retain the magnetically responsive substance 42 near to the coil 34. The magnetically responsive substance 42 may comprise micro-bubbles that will destruct and disburse when subjected to ultrasonic pulses from the transducer 35, and includes at least one of a group of magnetically responsive material consisting of magnetite, iron, iron oxide, cobalt, or other magnetic compounds. The micro-bubbles may also comprise substances, such as anti-cancer drugs or a modified gene for gene therapy, for example, that may be disbursed into tissues within the subject's body for treating an affected target area. The micro-bubbles 42 preferably will destruct and disburse when subjected to ultrasonic pulses in the range of 1 to 40 MHz, which are preferably generated by the transducer 35 when powered by an alternating current voltage at the required transducer excitation frequency. With the aid of an external magnetic field source, a magnetic field 30 may be applied to the distal end of the medical device 20. The applied magnetic field will cause the magnetically responsive element 28 to orient the distal end of medical device 20 and force the portion of the elongate medical device 20 including the coil 34 against the side wall 50 of a vessel, as shown in FIG. 1. The medical device 20 may be constructed with a preferential bend direction so that the application of a magnetic field causes the device to bend in a predetermined manner. This helps ensure that the coil 34 and the transducer 35 are properly positioned. The medical device 20 accordingly provides for navigation within the vasculature system of a subject body, to allow for placement of a coil disposed on the medical device against a target tissue surface within the subject's body for subsequent delivery of a magnetically responsive substance to the target tissue.

In one embodiment of an elongate medical device for delivering a magnetically responsive substance, the medical device comprises a tubular member having a proximal end, a distal end, and at least one magnetically responsive element disposed at the distal end of the tubular member. The medical device further comprises a coil disposed on the side of the tubular member that is spaced proximally from the magnetically responsive element. The coil is preferably spaced from the magnetically responsive element by a distance that is effective to reduce interference with an external magnetic field applied to the magnetically responsive element. The coil generates a field that attracts and collects magnetically responsive substances that are inserted within the body when a direct or alternating current voltage is applied to the coil. Upon application of a high frequency excitation voltage the transducer generates ultrasonic vibrations that disburse the collected magnetically responsive substances into the surrounding tissue. In one preferred embodiment the transducer is parallel to and supported a small distance from the coil to permit a passage of micro bubble particles to and through the coil. The ultrasonic vibrations are preferably generated by the transducer 35 when powered by an alternating current voltage having a frequency of about 20 MHz. The transducer is preferably used to generate a short burst of ultrasound for a time period of at least several seconds.

In the embodiment shown in FIG. 1, the medical device 20 comprises a recessed area (defined by elements 41 and 43 as shown in FIG. 1) on the side of the tubular member spaced proximally from the magnetically responsive element, wherein the coil is received in the recessed area. The coil 34 may be secured within the recess area, and may be at least partially embedded within the tubular member of the elongate medical device 20. The coil 34 further includes wires 36 and 38 extending through the lumen 26 of the tubular member. Wires 36 and 38 extend through the medical device 20 to the proximal end 24 outside of the subject's body, where a voltage 52 may be applied via control 54 to the wires 36 and 38 and accordingly the coil 34. When a voltage is applied to the coil 34, the coil attracts the magnetically responsive substance 42. A magnetic substance such as magnetite may be coated onto the micro-bubble shells, or magnetic particles inserted within the shell. When an AC voltage 56 is applied via control 54 to the transducer through wires 37 and 39, it generates an ultrasound burst that destructs the micro-bubbles. The ultrasound burst will cause the micro-bubbles 42 (as shown in FIG. 2) to destruct or explode, and the recessed area provides shaping for directing the explosion towards the target tissue to disburse the substance towards the target. The device is preferably construed to bend in the vicinity of the recess, so that the recess is held closely adjacent the curves of the vessel. In one embodiment, and as shown in FIG. 1, the distal end 22 of the tubular element is closed by capping element 32 to prevent delivering the micro bubbles and magnetically responsive substance in the vicinity of magnetic tip element 28. The capping element 32 may further comprise a self closing aperture appropriate for insertion of medical device 20 over a guide wire and designed to reduce or eliminate micro bubble or substance leakage from the device lumen distal end 22 to the blood vessel.

Figure 3:
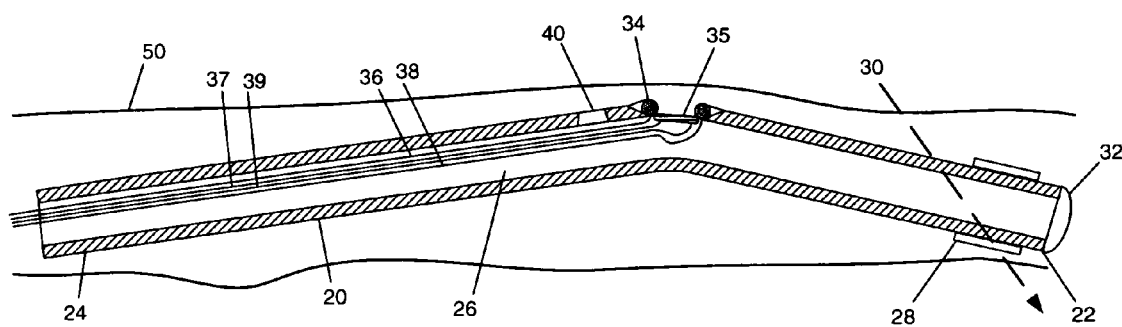
FIG. 3 shows a cross-sectional view of an alternate embodiment of the present invention with an aperture in the tubular element located proximally from the coil for upstream delivery of a magnetically responsive substance.
Figure 4:
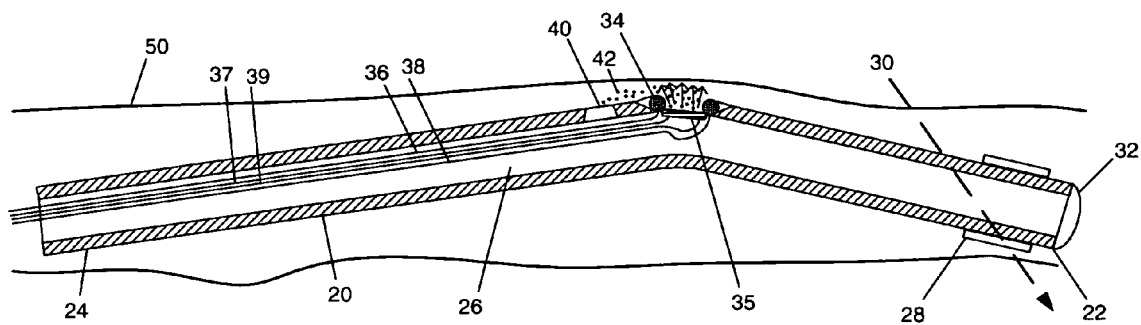
FIG. 4 shows a magnetically responsive substance being delivered through the embodiment of FIG. 3.

In other embodiments used where the blood velocity is very low, and as illustrated in FIG. 3, the medical device may further comprise an opening 40 in the tubular member near to the coil 34 through which a magnetically responsive substance may be delivered and injected into the patient's vasculature. In this embodiment the particles will not be swept away from the ultrasound impaction region. FIG. 4 illustrates the process of transfection using the embodiment of FIG. 3. In some cases this embodiment may be used in faster flowing vessels wherein the ultrasound bursts can be timed with release of particles into the region of the opening 40.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A medical device for delivering a magnetically responsive substance that is inserted within a subject body, the apparatus comprising:
   a tubular member having a proximal end, a distal end, and at least one magnetically responsive element disposed at the distal end of the tubular member;
   a coil disposed on the side of the tubular member and spaced proximally from the magnetically responsive element, where the coil is configured to generate a field that attracts and collects a magnetically responsive substance inserted within the body when a voltage is applied to the coil;
   a transducer disposed on a distal end portion of the medical device near the coil to generate ultrasonic vibration that disburses the magnetically responsive substance that was collected by the coil into the surrounding tissue when a high frequency alternating current voltage is applied to the transducer.

2. The medical device of claim 1 wherein the coil is spaced from the magnetically responsive element by a distance that is effective to reduce interference from a magnetic field applied to the magnetically responsive element.

3. The medical device of claim 1 further comprising an outlet adjacent the coil for injecting the magnetically responsive substance through the coil.

4. The medical device of claim 1 further comprising a passage through the tubular member, the passage communicating with an opening in the tubular member adjacent the coil, for injecting a magnetically responsive substance.

5. The medical device of claim 1, wherein the distal end of the tubular member is at least partially closed.

6. The medical device of claim 5, further comprising a closing element in the distal end of the device, the closing element having an aperture for receiving a guide wire.

7. A medical device for delivering a magnetically responsive substance that is inserted within a subject body, the apparatus comprising:
   a tubular member having a proximal end, a distal end, and at least one magnetically responsive element disposed at the distal end of the tubular member;
   a coil disposed on the side of the tubular member and spaced proximally from the magnetically responsive element, where the coil generates a field that attracts and collects a magnetically responsive substance inserted within the body when a voltage is applied to the coil:
   a transducer disposed near the coil to generate ultrasonic vibration that disburses the magnetically responsive substance that was collected by the coil into the surrounding tissue when a high frequency alternating current voltage is applied to the transducer, and
   a recessed area on the side of the tubular member spaced proximally from the magnetically responsive element, wherein the coil is disposed adjacent to the recessed area.

8. A medical device for delivering a magnetically responsive substance that is inserted within a subject body, the apparatus comprising:
   a tubular member having a proximal end, a distal end, and at least one magnetically responsive element disposed at the distal end of the tubular member;
   a coil disposed on the side of the tubular member and spaced proximally from the magnetically responsive element, where the coil generates a field that attracts and collects a magnetically responsive substance inserted within the body when a voltage is applied to the coil;
   a transducer disposed near the coil to generate ultrasonic vibration that disburses the magnetically responsive substance that was collected by the coil into the surrounding tissue when a high frequency alternating current voltage is applied to the transducer, where the coil is at least partially embedded within the tubular member.

9. A medical device for delivering a magnetically responsive substance that is inserted within a subject body, the apparatus comprising:
   a tubular member having a proximal end, a distal end, and at least one magnetically responsive element disposed at the distal end of the tubular member;
   a coil disposed on the side of the tubular member and spaced proximally from the magnetically responsive element, where the coil generates a field that attracts and collects a magnetically responsive substance inserted within the body when a voltage is applied to the coil;
   an outlet adjacent the coil for injecting the magnetically responsive substance through the coil; and
   a transducer disposed near the coil to generate ultrasonic vibration that disburses the magnetically responsive substance that was collected by the coil into the surrounding tissue when a high frequency alternating current voltage is applied to the transducer, wherein the magnetically responsive substance comprises micro-bubbles that destruct and disburse when subjected to ultrasonic pulses.

10. A system for attracting a magnetically responsive substance that is inserted into a subject's body towards a target area to treat the target area within the body with the magnetically responsive substance, the system comprising:
(a) an elongate medical device having a proximal end, a distal end, and at least one magnetically responsive element disposed at the distal end of the medical device that may be oriented in a desired direction by an external magnetic field applied to the distal end of the medical device;
(b) a coil disposed on the side of the elongate medical device, the coil being spaced proximally from the distal end so as to reduce interference from the external magnetic field applied to the magnetically responsive element of the elongate device (a);
(c) a voltage source for the coil;
(d) a transducer disposed near the coil;
(e) a high frequency alternating voltage source; and
(f) a control device for controlling the application of voltage to the coil and the alternating current voltage to the transducer,
wherein the control device (f) provides for applying a voltage from source (c) to the coil (b) to attract and collect a magnetically responsive substance inserted into the body around the coil, and the control device (f) provides for applying a high frequency alternating current voltage from source (e) to the transducer (d) to ultrasonically disperse the magnetically responsive substance that was collected by the coil into the tissue adjacent the coil.

11. The system of claim 10 wherein the elongate medical device further comprises a recessed area on the side of the tubular member adjacent the coil.

12. The system of claim 10 where the coil is at least partially embedded within the tubular member.

13. The system of claim 10 wherein the magnetically responsive substance that is inserted into the subject's body is delivered through the elongate medical device.

14. The system of claim 10, wherein the distal end of the elongate device is at least partially closed, and the at least partially closed distal end comprises an aperture for insertion of the medical device over a guide wire.

15. The system of claim 10 wherein the magnetically responsive substance is comprised of micro-bubbles that destruct and disburse when subjected to ultrasonic pulses.

16. The system of claim 10 wherein the ultrasonic pulses are produced by the high frequency alternating-current voltage source, and have a frequency in the range of 1 MHz and 40 MHz.

17. A method for delivering a magnetically responsive substance injected within a subject body to a target area within the subject body, the method comprising:
introducing into a subject body a medical device having a proximal end, a magnetically navigable distal end and a coil proximally spaced from the distal end;
magnetically navigating the distal end of the medical device in the subject body to a position where the coil on the medical device is adjacent the target tissue area in the subject body;
inserting a magnetically responsive substance at the medical device proximal end for delivery into the subject body near the target tissue area;
applying a voltage to the coil on the medical device for attracting a magnetically responsive substance that was inserted for delivery into the subject body towards the coil on the medical device; and
applying a high frequency alternating current voltage to a transducer in the medical device to ultrasonically disburse the magnetically responsive substance collected around the coil into the surrounding target tissue in the subject's body.

18. The method of claim 17 wherein the step of inserting a magnetically responsive substance comprises delivering the magnetically responsive substance through the elongate medical device to an opening in the coil aperture.

19. The method of claim 17 wherein the step of inserting a magnetically responsive substance comprises inserting the magnetically responsive substance into the vasculature system within the subject's body upstream from the desired target tissue.

20. The method of claim 17 where there is a recess in the sidewall of the elongate metical device, and magnetically navigating the distal end portion comprises applying a magnetic field to cause the distal end portion of the elongate medical device to align with the direction of the magnetic field and bend in such a way as to bring the recess in close proximity to the wall of the vessel, so that when the distal end portion of the device is bent, the recess defines a space between the elongate medical device and the wall of the vessel.

* * * * *

UNITED STATES PATENT AND TRADEMARK OFFICE
CERTIFICATE OF CORRECTION

PATENT NO. : 7,662,126 B2
APPLICATION NO. : 11/514690
DATED : February 16, 2010
INVENTOR(S) : Francis M. Creighton, IV It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 781 days.

Signed and Sealed this

Thirtieth Day of November, 2010

David J. Kappos
*Director of the United States Patent and Trademark Office*